(12) United States Patent
Payne et al.

(10) Patent No.: US 6,236,951 B1
(45) Date of Patent: May 22, 2001

(54) SENSOR INTERROGATION

(75) Inventors: Peter Alfred Payne, Knutsford; Krishna Chandra Persaud, Cheadle; Mohammed El Hassan Amrani, Brunswick, all of (GB)

(73) Assignee: Osmetech PLC, Cheshire (GB)

( * ) Notice: Subject to any disclaimer, the term of this patent is extended or adjusted under 35 U.S.C. 154(b) by 0 days.

(21) Appl. No.: 09/068,830

(22) PCT Filed: Nov. 18, 1996

(86) PCT No.: PCT/GB96/02834

§ 371 Date: May 15, 1998

§ 102(e) Date: May 15, 1998

(87) PCT Pub. No.: WO97/18467

PCT Pub. Date: May 22, 1997

(30) Foreign Application Priority Data

Nov. 16, 1995 (GB) .................................................. 9523406

(51) Int. Cl.⁷ ............................ G06F 19/00; G01N 27/00
(52) U.S. Cl. ................................ 702/116; 702/27; 702/77; 708/200; 708/813; 422/98
(58) Field of Search .................................. 702/75, 76, 77, 702/112, 116, 27; 370/208–210, 478; 708/200, 250, 400, 404, 813; 422/83, 94, 98

(56) References Cited

U.S. PATENT DOCUMENTS

| | | | |
|---|---|---|---|
| 3,691,364 | 9/1972 | Baba et al. ............................ | 235/181 |
| 5,045,285 * | 9/1991 | Kolesar, Jr. ............................. | 422/98 |
| 5,610,908 * | 3/1997 | Shelswell et al. .................... | 370/210 |
| 5,614,834 * | 3/1997 | Black et al. .......................... | 708/191 |
| 5,870,405 * | 2/1999 | Hardwick et al. .................... | 708/203 |
| 5,918,257 * | 6/1999 | Mifsud et al. ....................... | 73/31.05 |

FOREIGN PATENT DOCUMENTS

| | | | |
|---|---|---|---|
| 0387100 | 9/1990 | (EP) | ................................. F02P/5/15 |
| 2203553 | 10/1988 | (GB) | ............................. G01N/27/12 |
| 5296908 | 11/1993 | (JP) . | |

OTHER PUBLICATIONS

Z X Ding and P A Payne, "A New Golay Code System for Ultrasonic Pulse Echo Measurements", Meas. Sci. Technol. 1 (1990), pp. 158–165, 1990.*

Persaud et al., "Design Strategies for Gas and Odour Sensors Which Mimic the Olfactory System", Robots and Biological Systems: vol. 102, 1993, pp 579–602.

Ding et al. "A New Golay Code System for Ultrasonic Pulse Echo Measurements", Meas. Sci. Technol. 1, 1990, pp 158–165.

* cited by examiner

Primary Examiner—Marc S. Hoff
Assistant Examiner—Bryan Bui
(74) Attorney, Agent, or Firm—Christie, Parker & Hale, LLP

(57) ABSTRACT

There is disclosed a method for interrogating a sensor comprising the steps: applying a periodic electrical signal to the sensor; obtaining a signal therefrom; and performing an operation on the obtained signal to obtain the sensor response at a plurality of frequencies, said operation including a transformation to the frequency domain of said signal or a quantity related to said signal.

32 Claims, 10 Drawing Sheets

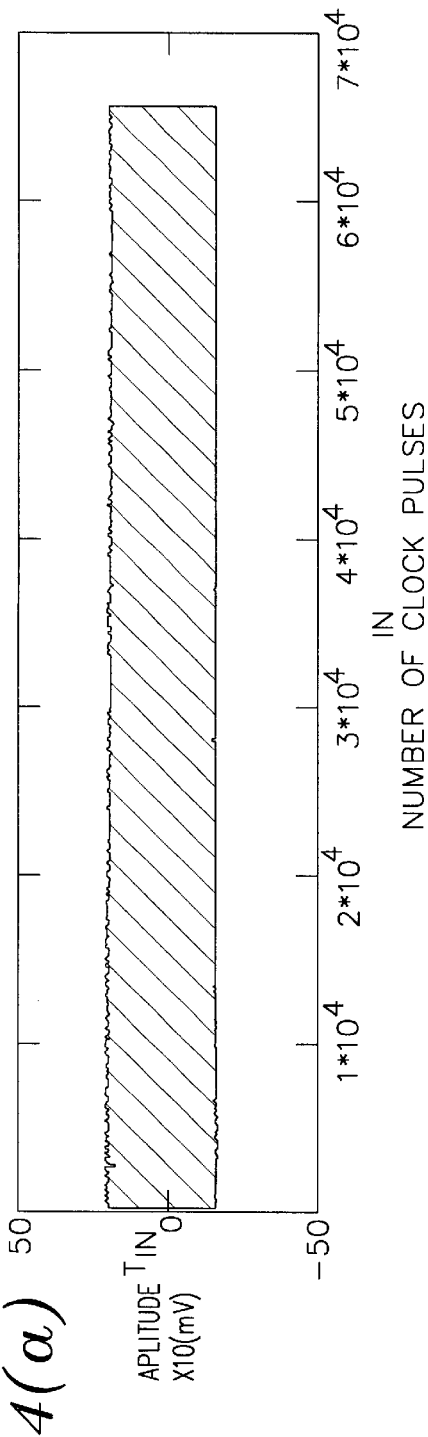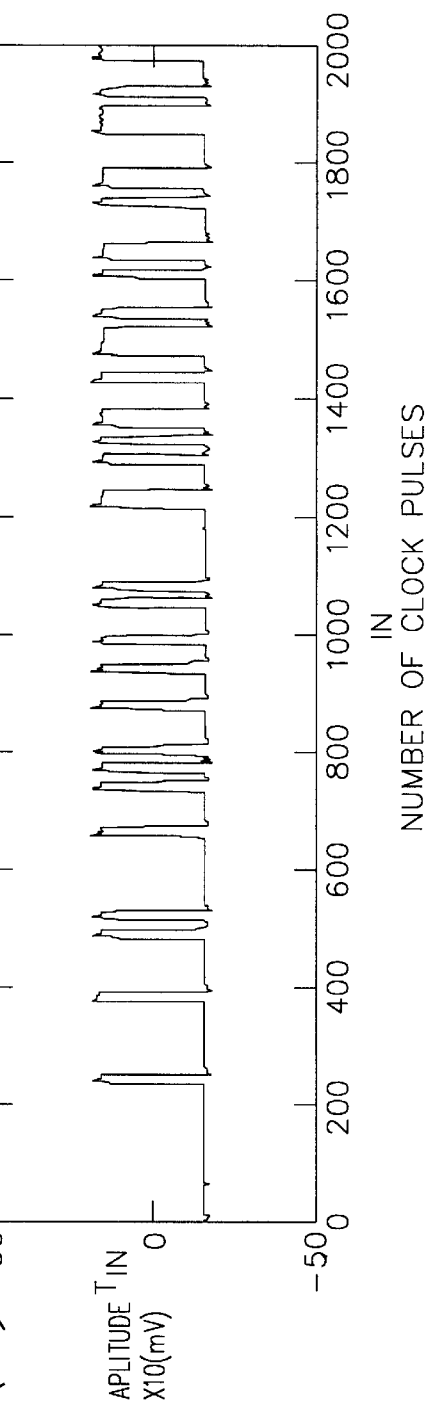
FIG. 4

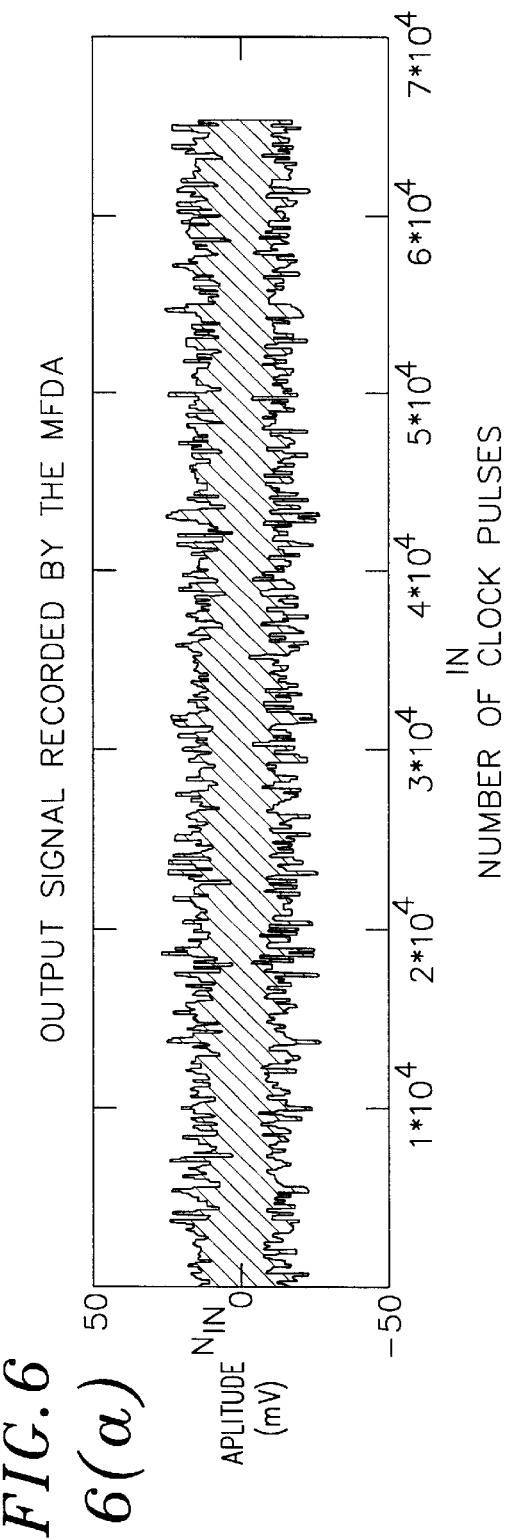
FIG. 6
6(a)
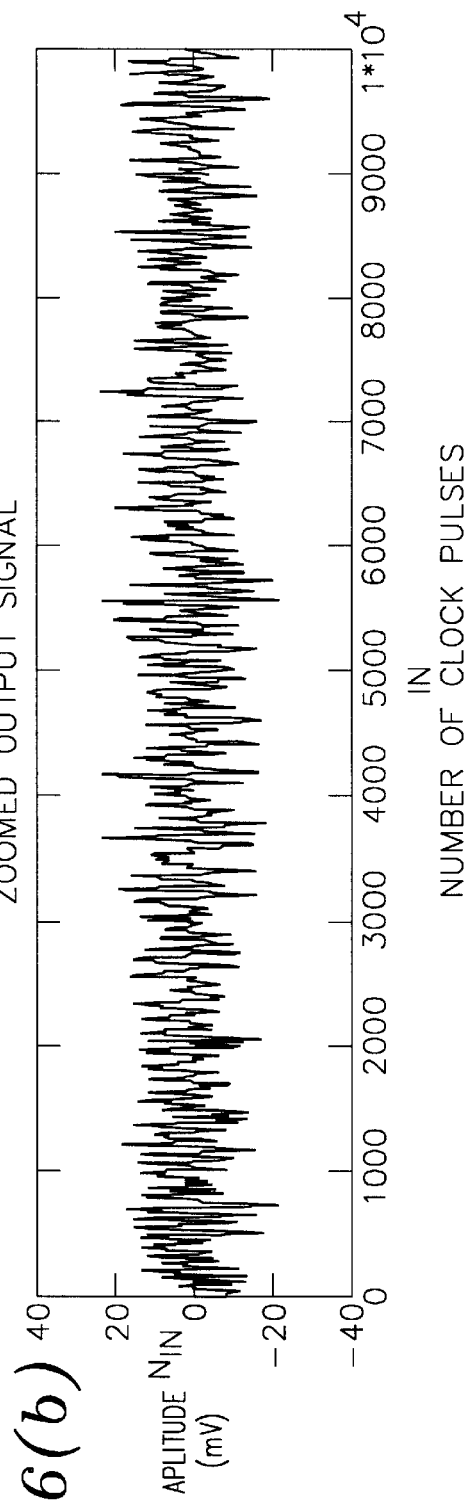
6(b)

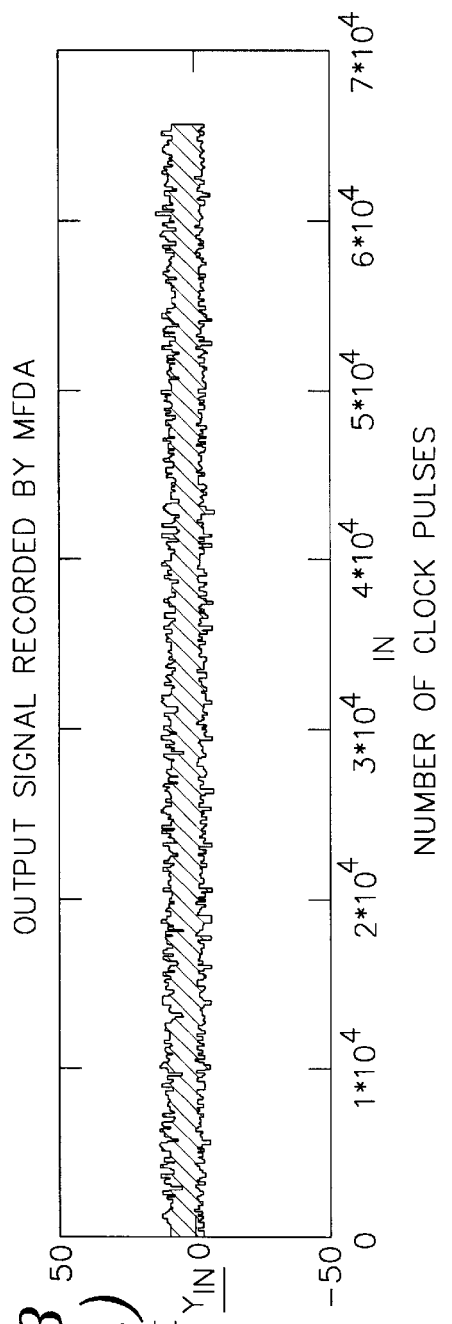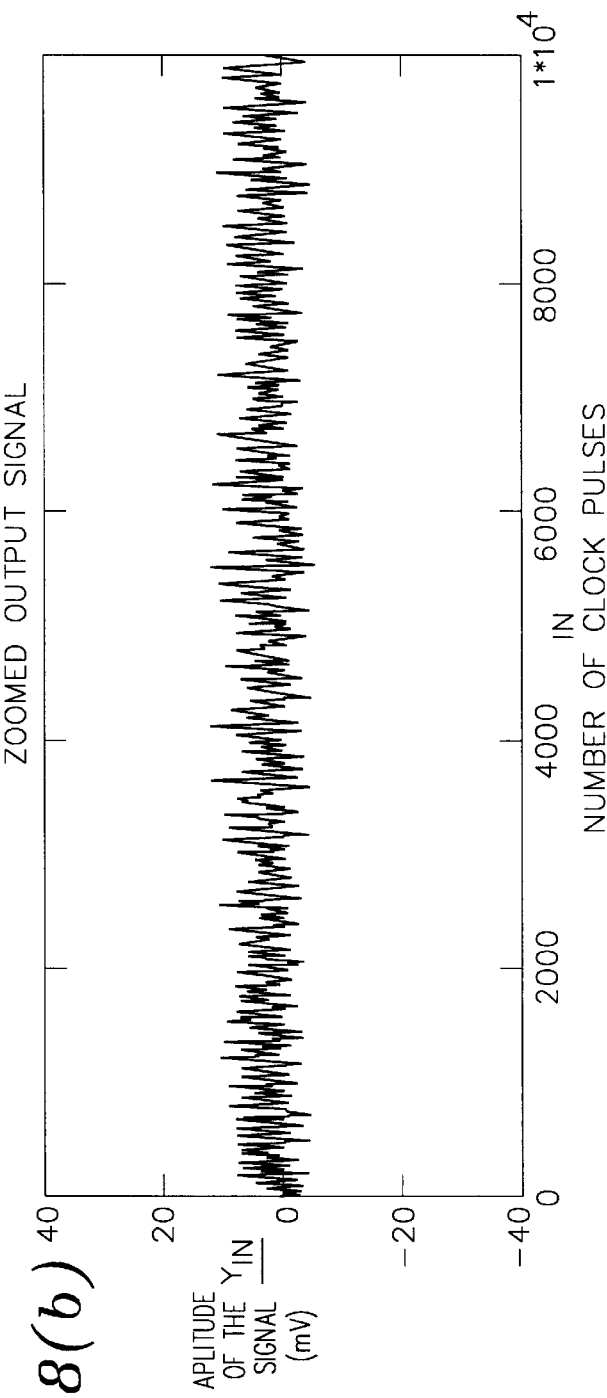
FIG. 8

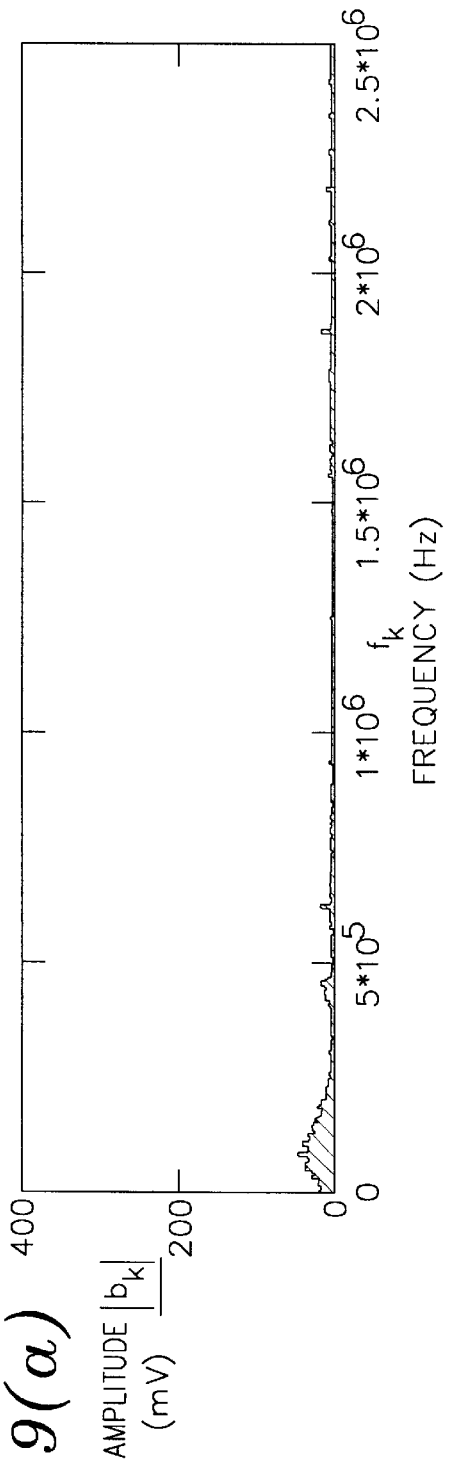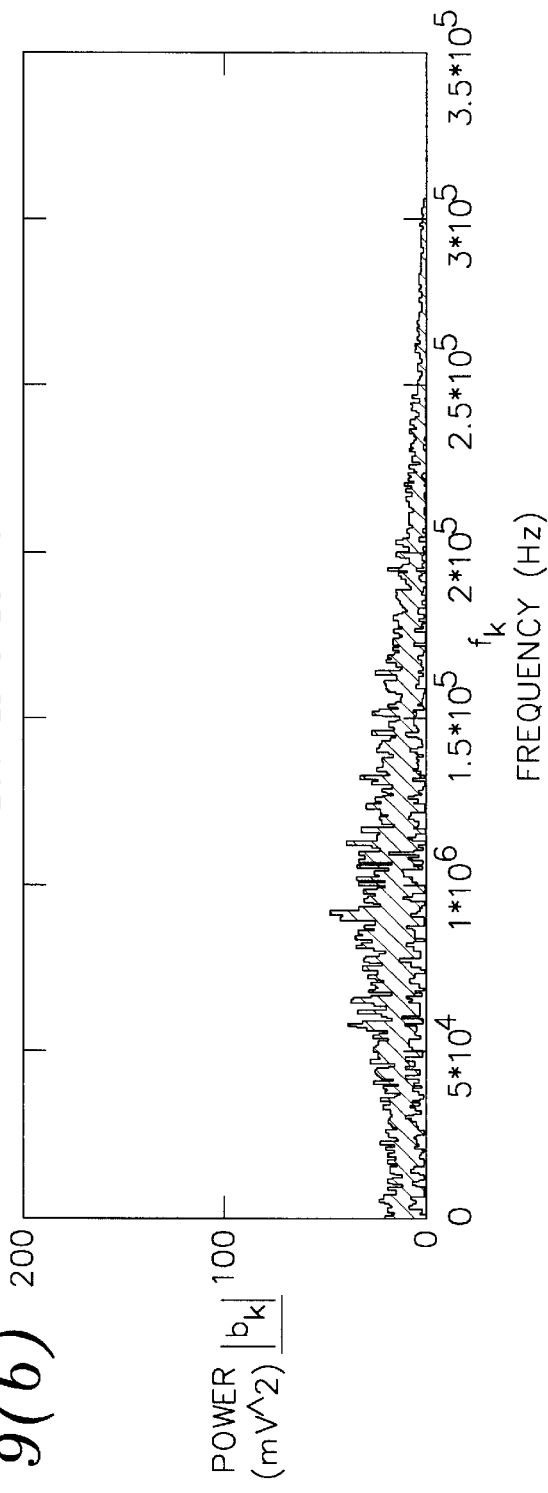
FIG. 9
9(a)
9(b)

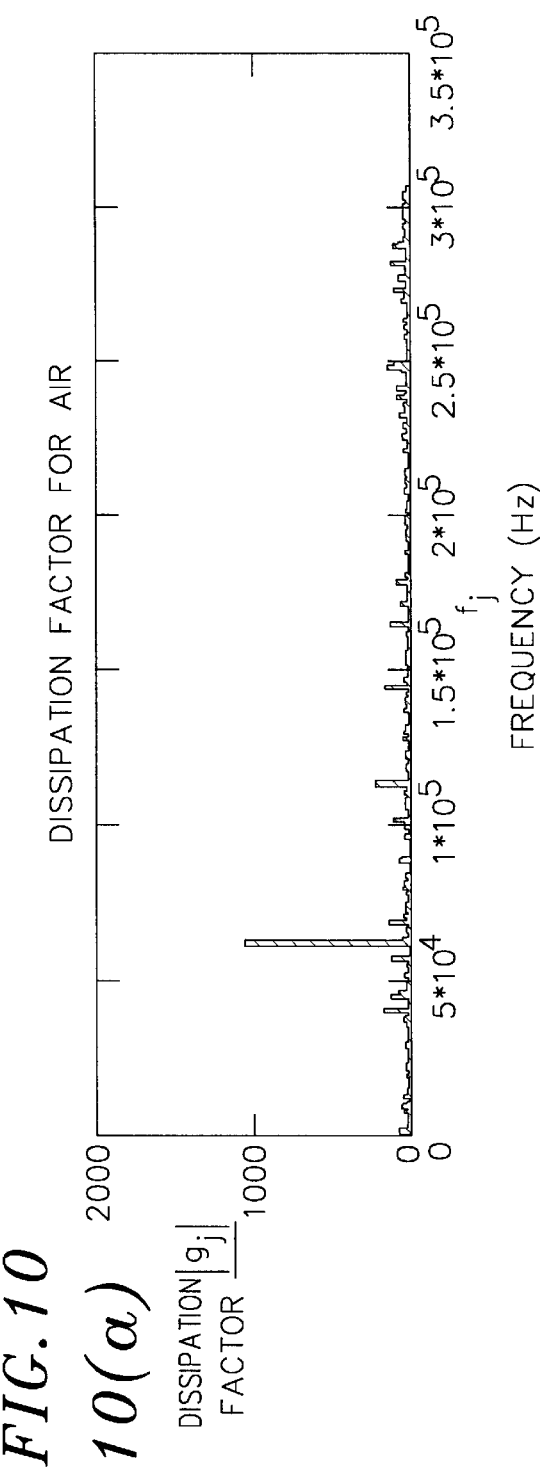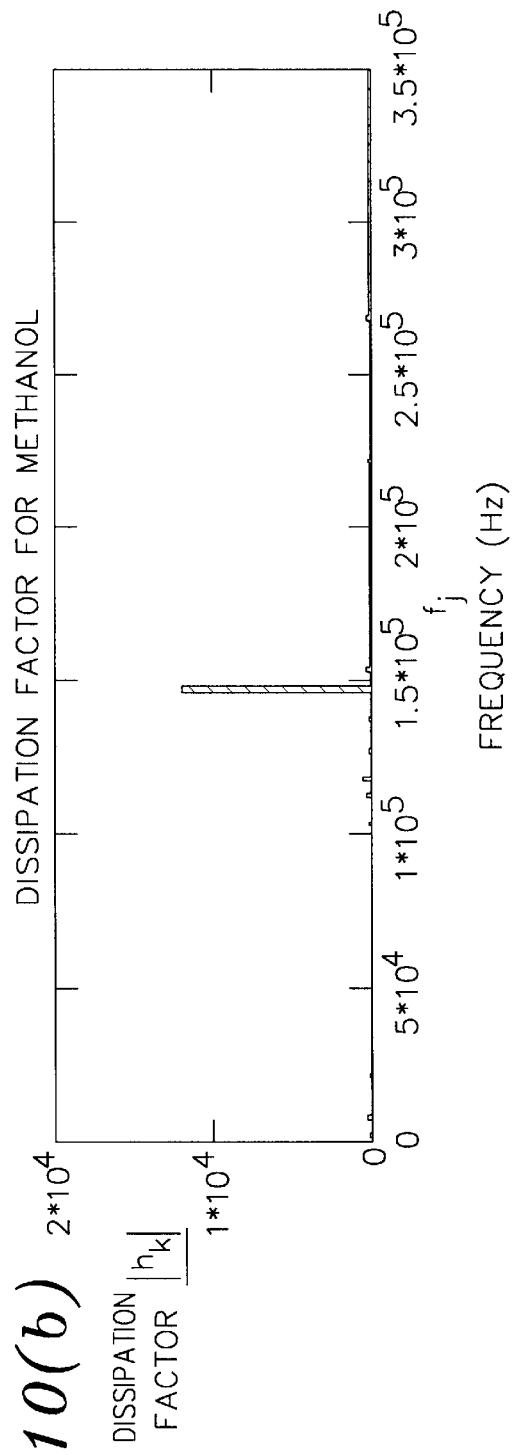
FIG. 10
10(a) 10(b)

SENSOR INTERROGATION

BACKGROUND OF THE INVENTION

This invention relates to a method and apparatus for the interrogation of sensors, with particular—but by no means exclusive—reference to semiconducting organic polymer based gas sensors.

There is a great deal of current interest in the use of semiconducting organic polymers in gas sensing applications, since such polymers display rapid gas adsorption/desorption kinetics, relatively high sensitivities and responses which broadly mimic the response of the human olfactory system (see, for example, Persaud K C, Bartlett J G and Pelosi P, in 'Robots and Biological Systems: Towards a new bionics?', Eds. Dario P, Sandini G and Aebisher P, NATO ASI Series F: Computer and Systems Sciences 102 (1993) 579). A typical sensor comprises a pair of electrodes bridged by at least one layer of semiconducting organic polymer; transduction is usually accomplished by measuring changes in the dc resistance of the sensors, these changes being induced by adsorption of gaseous species onto the polymer.

SUMMARY OF THE INVENTION

British Patent GB 2 203 553 discloses an improved interrogation method whereby an ac electric signal is applied to the sensor, and changes in an ac impedance quantity, such as resistance, reactance, or capacitance, are measured as a function of ac frequency. One advantage of this approach is the increase in the information derived from a single sensor: in contrast to the single measurement made with the dc transduction technique, a plurality of measurements are made (at a variety of ac frequencies). However, sweeping the ac frequency is a relatively cumbersome process, requiring an expensive Impedance Analyser.

The present invention provides an improved means of performing multifrequency measurements of sensors in which time domain measurement techniques are accompanied by an appropriate transformation to the frequency domain.

According to one aspect of the invention there is provided a method for interrogating a sensor comprising the steps of:

applying a periodic electrical signal to the sensor;

obtaining a signal therefrom; and performing an operation on the obtained signal to obtain the sensor response at a plurality of frequencies, said operation including a transformation to the frequency domain of said signal or a quantity related to said signal.

The sensor may be a gas sensor and may comprise semiconducting organic polymer.

Alternatively, the gas sensor may be a metal oxide, bulk acoustic wave or surface acoustic wave device.

The periodic electrical signal may be a pseudo random binary signal (PRBS), which may be in the form of a m-sequence.

The periodic electrical signal may be a Golay code, a Walsh function or any related periodic code.

The operation may comprise a Fourier transformation.

Cross correlation may be employed in order to obtain the multifrequency sensor response function.

The sensor response may be obtained by coherent demodulation of said signal.

Alternatively, co-variance may be employed in order to obtain the multifrequency sensor response function.

According to a second aspect of the invention there is provided a sensor interrogation apparatus comprising:

periodic electrical signal generator means for applying a periodic electrical signal to said sensor;

signal collection means for obtaining an electrical signal from said sensor; and time to frequency domain transformation means arranged to transform the obtained electrical signal to the frequency domain.

The sensor may be a gas sensor, which may comprise semiconducting organic polymer.

Alternatively, the gas sensor may be a metal oxide, bulk acoustic wave or surface acoustic wave device.

The signal collection means may comprise a load resistor.

The time to frequency domain transformation means may comprise coherent demodulation means.

The time to frequency domain transformation may comprise computing means adapted to perform Fourier transformations.

The periodic electrical signal generator means may comprise a PRBS generator, which may itself comprise shift registers.

The periodic electrical signal generator means may comprise a Golay code, a Walsh function generator, or a generator generating any related periodic code.

BRIEF DESCRIPTION OF THE DRAWINGS

An embodiment of a method and apparatus according to the invention now be described with reference to the accompanying drawings, in which:

FIG. 4 shows a) the entire input PRBS and b) an expanded portion thereof;

FIG. 5 shows the Fourier transform of the input PRBS of FIG. 4a;

FIG. 6 shows a) the entire output PRBS when a sensor is exposed to air and b) an expanded portion thereof;

FIGS. 7a and 7b show Fourier transform spectra of the output PRBS of FIG. 6a;

FIG. 8 shows a) the entire output PRBS when a sensor is exposed to methanol vapour and b) an expanded portion thereof;

FIGS. 9a and 9b show Fourier transform spectra of the output PRBS of FIG. 8a; and FIG. 10 shows dissipation factors obtained when the sensor is exposed a) to air and b) to methanol vapour.

FIGS. 1 and 2 illustrate a method and apparatus for interrogating a sensor in which:

periodic electrical signal is applied to the sensor;

a signal is obtained therefrom; and said signal is coherently demodulated to obtain sensor responses at a plurality of frequencies.

DETAILED DESCRIPTION

Figure 1:
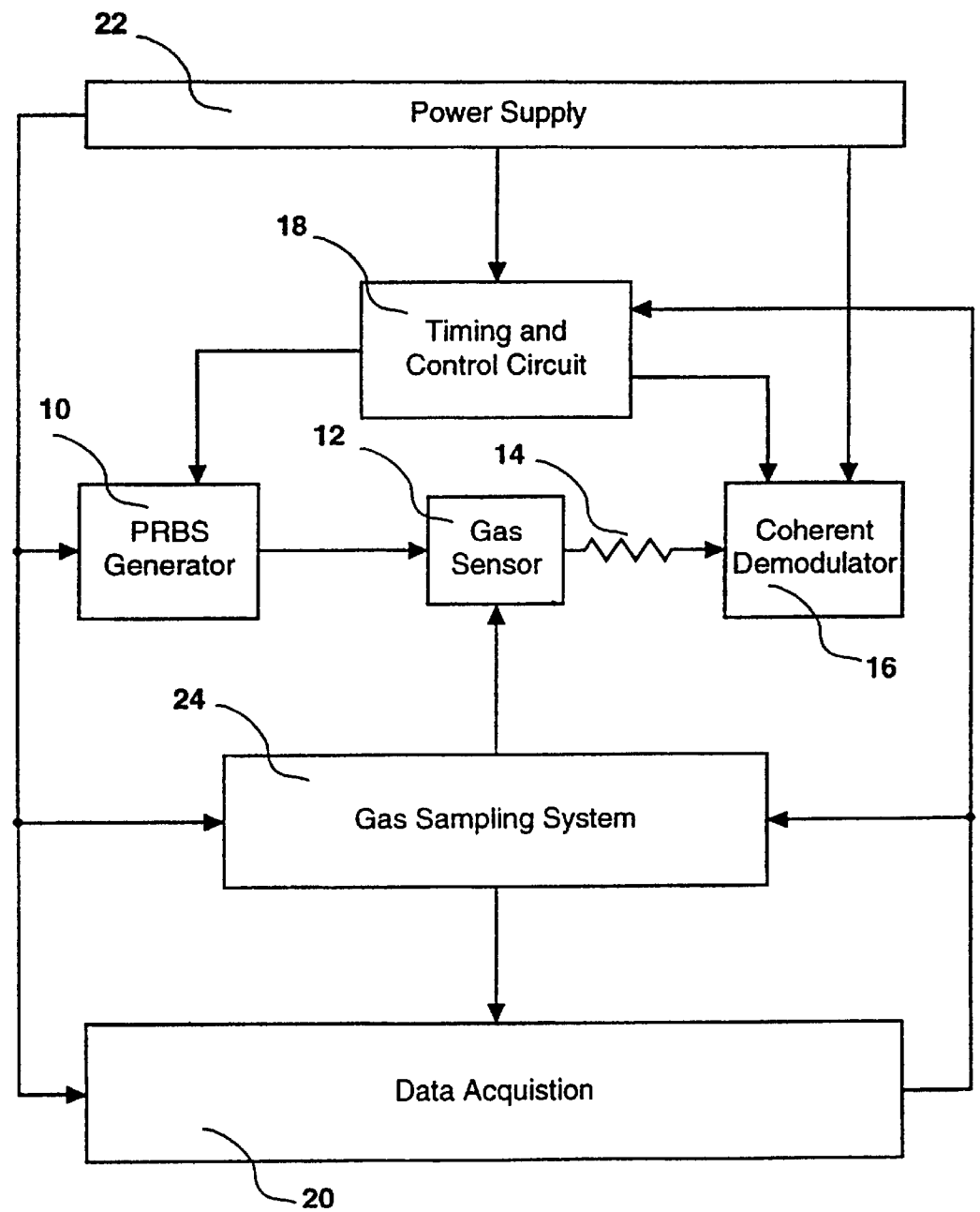
FIG. 1 shows a first embodiment of an interrogation apparatus.

FIG. 1 shows an interrogation system according to the invention for a gas sensor 12 comprising a PRBS generator 10, a load resistor 14 and a coherent demodulator 16. The system further comprises a timing and control circuit 18, data acquisition card 20, power supply 22 and gas sampling system 24.

The power supply 22 provides electrical power for the PRBS generator 10, coherent demodulator 16, timing and control circuit 18, data acquisition card 20 and gas sampling system 24. The timing and control circuit 18 provides stable clock pulses for the PRBS generator 10, and intermediate frequencies (defined below) for the coherent demodulator 16 via a crystal oscillator and programmable dividers (not shown). The circuit 18 further provides control signals to control the gas sampling system 24 and data acquisition card 20. The functions of the system are i) to deduce the multifrequency sensor 12 response and ii) to monitor changes in this response on exposure of the sensor 12 to a gas. The gas sampling system 24 permits such exposure of sensor 12 to a gas of interest, and allows purging of the sensor 12 and introduction of a reference gas (which may be the purging gas).

The PRBS generator 10 accepts clock pulses from the timing and control circuit 18 and generates a maximum length sequence (m sequence) of $N=2^n-1$ where n is an integer and is 4 in the present example. If the clock frequency is $f_c$ with a corresponding time interval $\Delta t$, then the PRBS generated has a period $T_o$ given by:

$$T_o = (2^n - 1)\Delta t \quad (1)$$

with a corresponding fundamental frequency $f_p$ given by:

$$f_p = \frac{f_c}{2^n - 1} \quad (2)$$

Intermediate, or overtone, frequencies $f_i$ are given by:

$$f_i = \frac{f_c}{i} \quad (3)$$

where $i=1,2,\ldots 2^n-2$.

In this first embodiment the PRBS generator 10 is a 4 bit parallel access shift register together with a quadruple 2-input exclusive—OR gate. The OR gate generates the input signal to the shift register by the exclusive—OR combination of the third and fourth bit of the shift register, and thus the circuit goes through a maximum of 15 states.

The PRBS generated thereby is applied to the sensor 12, which may be of the type wherein a layer of semiconducting organic polymer such as polypyrrole is deposited on and between two metal electrodes so as to effect an electrical connection. The signal across the load resistor 14 is then coherently demodulated at intermediate frequencies $$f_i = \frac{f_c}{i}$$

where $i=1,2\ldots 8$ (i.e. harmonics are taken up to −3 dB) by the coherent demodulator 16. The sensor response at these frequencies is obtained thereby.

Figure 2:
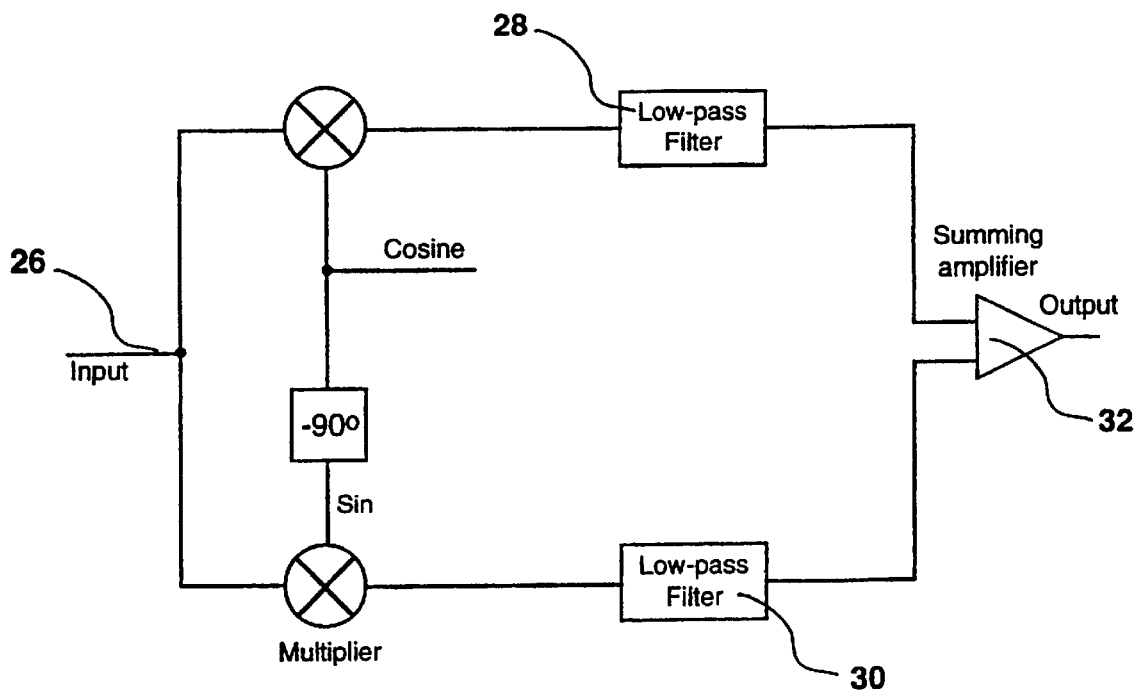
FIG. 2 shows a coherent demodulator.

A schematic diagram of the coherent demodulator (essentially a two channel cross correlation operator) is shown in FIG. 2. The input 26—the voltage across the load resistor 14—is multiplied in one channel by sin ($w_i$) and in a second channel by cos ($w_i$) where $w_i$ is the radian frequency corresponding to cyclical frequency $f_i$. These multiplication functions are performed by a quadrature amplitude modulator based on a programmable four channel operational amplifier. The modulated signals are low pass filtered by second order active low pass filters 28, 30, and added together with a summing operational amplifier 32.

The resulting output signal from the demodulator 16 is sampled at the appropriate rate, converted into a digital signal and loaded into memory by the data acquisition card 20. Data may be transferred therefrom into a computer for further processing and display. The demodulator 16 may be used to obtain the system response at a chosen frequency, or a set of lines may be selected and the demodulation performed in parallel. It may be possible to derive further information from phase angle data.

The two primary advantages of periodic signals are the ease with which they may be recognised in the presence of noise and the substantially unbiased estimate of the system response—in this case the multifrequency response of the sensor—which they provide. A particularly preferred embodiment of such periodic signals is a pseudorandom binary signal which, since its pulseform is deterministic, can be recreated as desired providing that the sequence start time and length are known.

The frequencies of the PRBS sequence are dictated by the gas sensor employed. Typically, frequencies in the range 0.1–1.0 MHz are required, but this range should not be considered a limiting one. Frequencies between $\mu$Hz to 100 MHz or greater may be routinely generated. The PRBS is preferably bipolar at voltage levels between±0.1 to 1.0.V, but this should not be considered a limiting requirement either.

Figure 3:
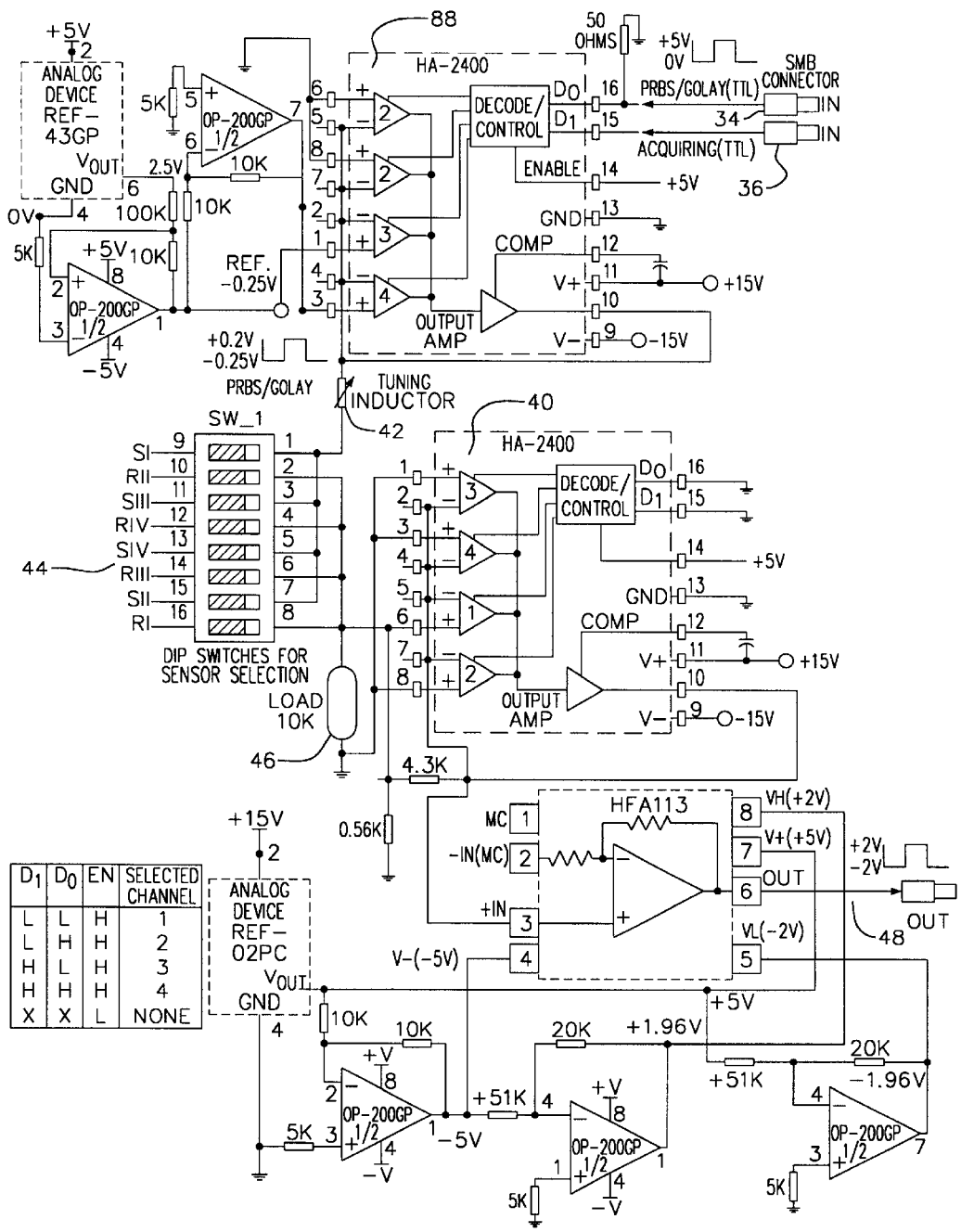
FIG. 3 is a circuit diagram of a multi-frequency data acquisition card.

In a second embodiment a 4 sensor semiconducting organic polymer array is connected to a multi-frequency acquisition card. FIG. 3 is a circuit diagram of the card. PRBS is generated by a PRBS generator (not shown) and input to the card via PRBS inlet 34 and acquiring inlet 36. The PRBS signal is at this stage in the form of 0–5V TTL signals. Circuitry 38 converts this input signal into a bipolar PRBS code of magnitude±0.25V. The use of bipolar signal is preferable since unipolar signal causes drift in sensor output.

Circuitry 40, which includes a tuning inductor 42 and DIP switches 44, controls the application of the PRBS to any selected sensor in the 4 sensor array (not shown). A voltage output from the selected sensor is obtained via a 10KΩ load resistor 46. Circuitry 48 produces a bipolar output of maximum range=2V. This output is taken across for storage on a computer. Subsequent analysis is also performed on the computer.

The computer also supports software which controls the system variables. In the present example 16 shift register stages are employed (tap point at the 4th stage) producing a sequence length of 65535 clock pulses. The ADC prescaler was set to 20 MHz acquisition frequency and a PRBS prescaler value of 8 was employed (i.e. the shift frequency was 2.5 MHz and each data point corresponds to 0.4 $\mu$s).

FIG. 4a shows the total PRBS applied to the gas sensor. At this scale, such a representation is not very revealing. FIG. 4b shows an expanded portion of the PRBS train.

Figure 5:
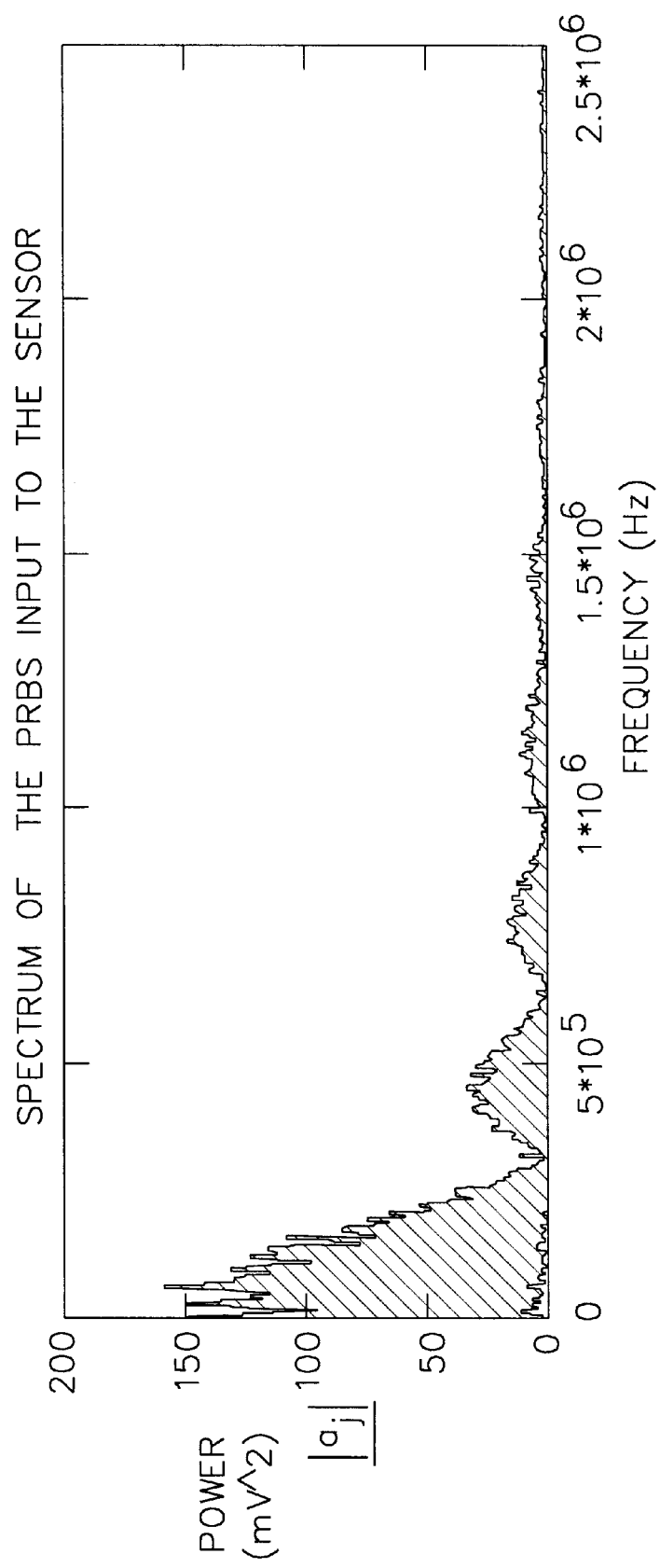

FIG. 5 shows the spectrum obtained when a fast Fourier Transformation (FFT) is performed on the PRBS of FIG. 4a by the computer. This is the frequency domain equivalent of the input to the sensor. The PRBS is intended to concentrate energy mainly in the region up to about 200 KHz.

Figure 7:
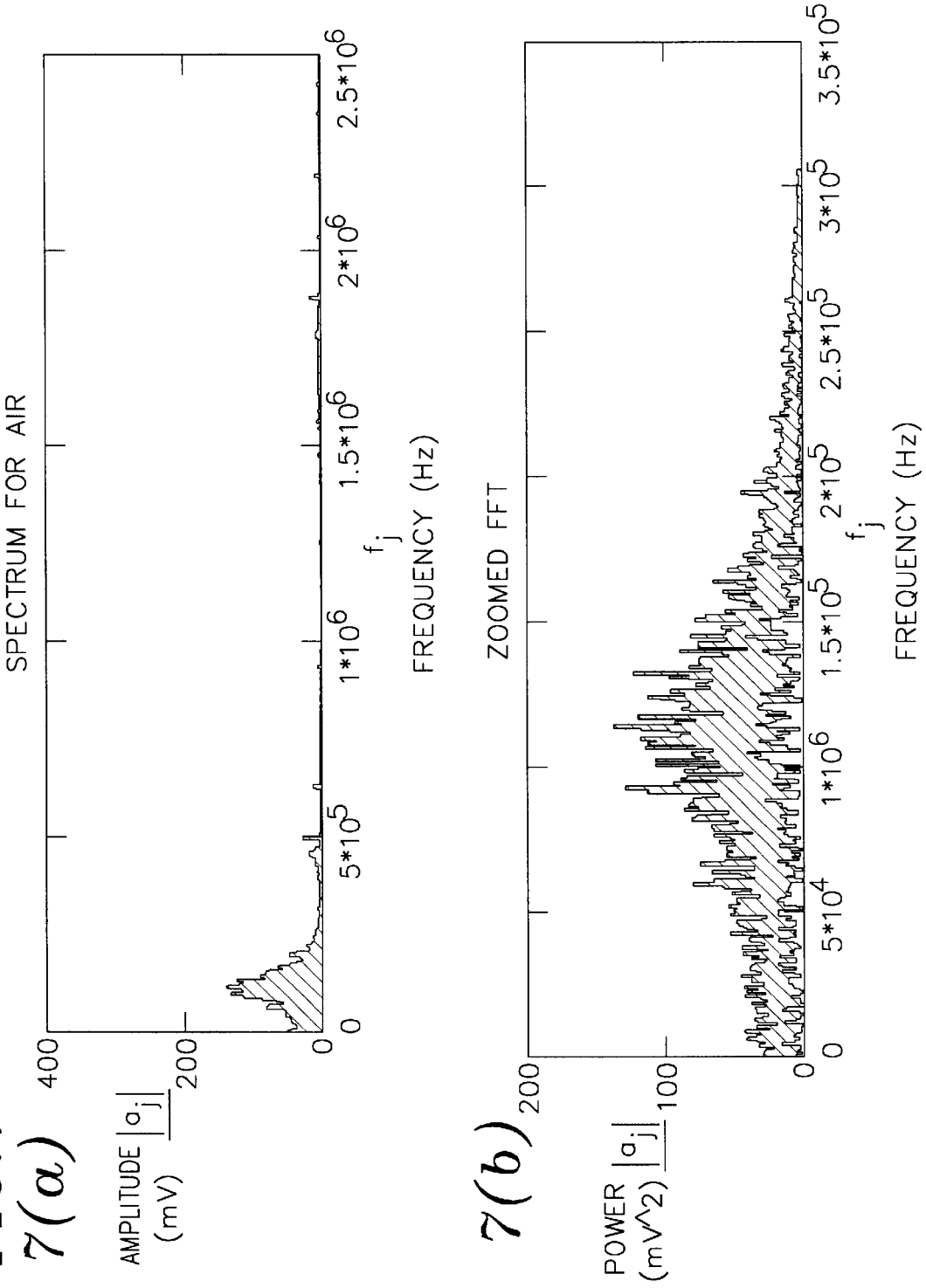

FIG. 6 shows the output from the sensors, measured across the load resistor 46, when the sensor is exposed to air (a gas sampling system similar to that described with regard to FIG. 1 is employed). FIG. 6a shows the complete PRBS output—which, even at this level of resolution is clearly different from the input signal of FIG. 4a—and FIG. 6b shows an expanded portion. Interestingly, the delta-function like spikes of the PRBS are now somewhat distorted in appearance : this is undoubtedly due to the finite inductance and capacitance of the sensor. FIGS. 7a and 7b show the frequency domain spectrum obtained by performing a FFT on the data of FIG. 6a.

FIGS. 8a and 8b show the time domain output signal obtained when the sensor is exposed to methanol vapour. FIGS. 9a and 9b show the corresponding frequency domain spectrum obtained when a FFT is performed on the output shown in FIG. 9a. Clearly the spectrum is different to the spectrum obtained in air (FIG. 7a), showing that this interrogation technique can produce gas sensitive data. Interestingly, the absolute power of the frequency spectrum of FIG. 9a, and the output signal amplitude of FIG. 8a are smaller than the corresponding values obtained with air. This is consistent with the increase in dc resistance obtained when the sensor is exposed to methanol using the prior art dc resistance interrogation technique.

FIGS. 10 and 10b show dissipation factors obtained, respectively, in air and methanol. The dissipation factor is obtained by dividing the real part of frequency response by the imaginary part of the response (plus an increment of 0.01 to prevent the occurence of a singularity). Distinctly different peak dissipation factors are obtained, viz, ca. 60 KHz for air and ca. 150 KHz for methanol.

It will be appreciated that it is not intended to limit the invention to the above examples only, many variations, such as might readily occur to one skilled in the art, being possible without departing from the scope thereof. For instance, other forms of periodic signals may be applied to the sensor. An example is a Golay code, which is a pair of complementary series exhibiting autocorrelation functions having self noise sidelobes of equal magnitude but opposite sign. The sum of the two individual autocorrelation functions is a close approximation to the ideal Dirac delta function (see, for example. Ding ZX and Payne Pa., Meas. Sci. Technol., 1 (1990) 158). Another example of a suitable periodic signal is a Walsh function.

It should be noted that other methods may be employed to derive the frequency domain response spectrum from the time domain PRBS interrogating sequence. One approach is to transform the time domain PRBS input x(t) and the sensor output y(t) to produce a frequency domain input X($\omega$) and output Y($\omega$). The sensor frequency response S($\omega$) is then given by:

$$S(\omega) = \frac{Y(\omega)X^*(\omega)}{X(\omega)X^*(\omega)} \quad (4)$$

Another approach is to cross correlate and auto-correlate in the time domain and to transform the correlations to the frequency domain to yield spectral density functions. If the auto-correlation function between sensor output and PRBS input at time difference $\tau$ is $R_{xy}(\tau)$, then the cross spectral density function $\Phi_{xy}(\omega)$ is given by:

$$\Phi_{xy}(\omega) = \int^R_{xy}(\tau)\exp(-i\omega\tau)\, d\tau \quad (5)$$

where in practice the upper and lower limits of the integral will be finite.

The system response S($\omega$) is now given by:

$$S(\omega) = \frac{\Phi_{xy}(\omega)}{\Phi_{xx}(\omega)} \quad (6)$$

where $\Phi_{xy}(\omega)$ is the power spectral density function. Appropriate transformations such as a fast Fourier transform (FFT) may be applied for these purposes. It may be desirable to compute the auto-correlation function between the sensor output when exposed to unknown gas and the sensor output in the presence of an air reference flow. Covariance techniques may be applied as an alternative to cross correlation.

It should be noted further that the present invention is not limited to semiconducting organic polymer based sensors, but rather, extends to any sensor which may be interrogated by application of multifrequency signals. Such sensors include any material that can be treated as a dielectrical and which is affected by its environment, such as metal oxides, non-polymer semiconductors and organic polymers which are not semiconducting. Bulk acoustic wave and surface acoustic wave devices are also within the scope of the invention. While gas sensing is of particular interest, it is possible to measure, using the methods and apparatus of the invention, the response of sensors to other influences, such as temperature and pressure, if they have any response thereto, either independently of or in conjunction with their possible response to the presence of a gas or mixture of gases. In any case, it is understood that the use of semiconducting organic polymer based sensors in gas sensing includes the detection of odours and volatile species, and, further, that such sensors may be employed in other applications, such as liquid phase analyte detection.

While the apparatus described with reference to the drawings is appropriate to a laboratory or field instrument, it is also possible to configure the sensor for example as a smart tag which could be included in food packaging and scanned using electromagnetic radiation techniques to reveal its resonant frequency, which would be expected to change as the composition of gases changed within the packaging, which might reveal the age of the goods or some other factor such as whether the goods have been exposed to a temperature above the recommended storage temperature or if the package seal has failed.

Such sensors with their associated circuitry could be manufactured inexpensively and interrogated using a hand-portable scanning device for warehouse or supermarket use. The scanning device could comprise a database showing the expected response of various sensors—sensors used for meat products, for example, might be quite different and have a different characteristic response from sensors used for dairy products or packed vegetables.

While a system as described involving time to frequency domain transformation means would be very appropriate in the analysis of signals emitted by such smart tags in response to an interrogation signal, it may well be the case that the smart tags could incorporate some analytical circuitry that emitted—or failed to emit—a recognisable signal consequent upon some change in the sensor's environment, and such other analysis method could be used independently of or in conjunction with the time to frequency transformation based analysis of the present invention.

What is claimed is:

1. A method for interrogating a sensor comprising the steps:

applying a periodic coded electrical signal to the sensor, said periodic coded signal being characterized in that the periodic signal is a pseudo random binary signal, a Golay code, a Walsh function or a related periodic code;

obtaining a signal therefrom; and performing an operation on the obtained signal to obtain the sensor response at a plurality of frequencies, said operation including a transformation to the frequency domain of said signal or a quantity related to said signal.

2. A method according to claim 1 in which the sensor is a gas sensor.

3. A method according to claim 2 in which the gas sensor comprises semiconducting organic polymer.

4. A method according to claim 2 in which the gas sensor is a metal oxide, bulk acoustic wave or surface acoustic wave device.

5. A method according to claim 1 in which the periodic coded electrical signal is pseudo random binary signal.

6. A method according to claim 5 in which the pseudo random binary signal is in the form of a m sequence.

7. A method according to claim 1 in which the periodic coded electrical signal is Golay code, a Walsh function or any related periodic code.

8. A method according to claim 1 in which the operation comprises a Fourier transformation.

9. A method according to claim 1 in which cross correlation is employed in order to obtain the multifrequency sensor response function.

10. A method according to claim 1 in which the sensor response is obtained by coherent demodulation of said signal.

11. A method according to claim 1 in which co-variance is employed in order to obtain the multifrequency sensor response function.

12. A sensor interrogation apparatus comprising:

a sensor;

periodic electrical signal generator means for applying a periodic coded electrical signal to said sensor;

signal collection means for obtaining an electrical signal from said sensor;

time to frequency domain transformation means arranged to transform the obtained electrical signal to the frequency domain;

characterized in that the periodic signal is a pseudo random binary signal, a Golay code, a Walsh function or a related periodic code.

13. Apparatus according to claim 12 in which the sensor is a gas sensor.

14. Apparatus according to claim 13 in which the gas sensor comprises semiconducting organic polymer.

15. Apparatus according to claim 13 in which the gas sensor is a metal oxide, bulk acoustic wave or surface acoustic wave device.

16. Apparatus according to claim 12 in which the signal collection means comprises a load resistor.

17. Apparatus according to claim 12 in which the time to frequency domain transformation means comprise coherent demodulation means.

18. Apparatus according to claim 12 in which the time to frequency domain transformation means comprise computing means adapted to perform Fourier transformations.

19. Apparatus according to claim 12 in which the periodic electrical signal generator means comprises a pseudo random binary signal generator.

20. Apparatus according to claim 19 in which the pseudo random binary signal generator comprises shift registers.

21. Apparatus according to claim 12 in which the periodic electrical signal generator means comprises a Golay code generator, a Walsh function generator or a generator generating any related periodic code.

22. A method for interrogating a gas sensor comprising the steps:

applying a periodic coded electrical signal to the gas sensor, said periodic coded signal being characterized in that the periodic signal is a pseudo random binary signal, a Golay code, a Walsh function or a related periodic code;

obtaining a signal therefrom; and performing an operation on the obtained signal to obtain the gas sensor response at a plurality of frequencies, said operation including a transformation to the frequency domain of said signal or a quantity related to said signal.

23. A method according to claim 22 in which the gas sensor comprises semiconducting organic polymer.

24. A method according to claim 22 in which the gas sensor is a metal oxide, bulk acoustic wave or surface acoustic wave device.

25. A method according to claim 22 in which the periodic coded electrical signal is a pseudo random binary signal.

26. A method according to claim 22 in which the periodic coded electrical signal is a Golay code, a Walsh function or any related periodic code.

27. A gas sensor interrogation apparatus comprising:

a gas sensor;

periodic electrical signal generator means for applying coded electrical signal to said sensor, said periodic signal being characterized in that the periodic signal is a pseudo random binary signal, a Golay code, a Walsh function or a related periodic code;

signal collection means for obtaining an electrical signal from said sensor; and time to frequency domain transformation means arranged to transform the obtained electrical signal to the frequency domain.

28. Apparatus according to claim 27 in which the gas sensor comprises semiconducting organic polymer.

29. Apparatus according to claim 27 in which the gas sensor is a metal oxide, bulk acoustic wave or surface acoustic wave device.

30. Apparatus according to claim 27 in which the periodic electrical signal generator means comprises a pseudo random binary signal generator.

31. Apparatus according to claim 30 in which the pseudo random binary signal generator comprises shift registers.

32. Apparatus according to claim 27 in which the periodic electrical signal generator means comprises a Golay code generator, a Walsh function generator, or a generator generating any related periodic code.

* * * * *

UNITED STATES PATENT AND TRADEMARK OFFICE
CERTIFICATE OF CORRECTION

PATENT NO. : 6,236,951 B1
DATED : May 22, 2001
INVENTOR(S) : Peter Alfred Payne, Krishna Chandra Persaud and Mohammed El Hassan Amrani It is certified that error appears in the above-identified patent and that said Letters Patent is hereby corrected as shown below:

Title page,
Item [86], PCT No, § 371 Date and § 102(e) Date replace "May 15, 1998" with -- May 13, 1998 -- (both occurrences).

Signed and Sealed this

Tenth Day of September, 2002

Attest:

Attesting Officer

JAMES E. ROGAN
Director of the United States Patent and Trademark Office